US010729315B2

(12) United States Patent
Harrah et al.

(10) Patent No.: US 10,729,315 B2
(45) Date of Patent: Aug. 4, 2020

(54) MEDICAL RETRIEVAL DEVICES AND RELATED METHODS OF USE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Arpita Banerjee, Bangalore (IN); Sandesh Gavade, Bangalore (IN); Abhijit Takale, Pune (IN); Pavan Misra, Bangalore (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 547 days.

(21) Appl. No.: 15/413,994

(22) Filed: Jan. 24, 2017

(65) Prior Publication Data

US 2017/0215715 A1 Aug. 3, 2017

Related U.S. Application Data

(60) Provisional application No. 62/288,906, filed on Jan. 29, 2016.

(51) Int. Cl.
| | |
|---|---|
| *A61B 1/00* | (2006.01) |
| *A61B 1/04* | (2006.01) |
| *A61B 1/06* | (2006.01) |
| *A61B 90/30* | (2016.01) |
| *A61B 1/07* | (2006.01) |
| *A61B 1/307* | (2006.01) |
| *A61B 17/22* | (2006.01) |
| *A61B 90/00* | (2016.01) |

(52) U.S. Cl.
CPC ........ *A61B 1/0684* (2013.01); *A61B 1/00101* (2013.01); *A61B 1/0607* (2013.01);
(Continued)

(58) Field of Classification Search
CPC ....... A61B 5/1076; A61B 5/0084; A61B 1/07; A61B 5/1079; A61B 18/26;
(Continued)

(56) References Cited

U.S. PATENT DOCUMENTS

| 8,934,962 B2 | 1/2015 | Saadat et al. | |
|---|---|---|---|
| 2004/0242961 A1* | 12/2004 | Bughici | A61B 1/07 |
| | | | 600/108 |

(Continued)

FOREIGN PATENT DOCUMENTS

| EP | 1 867 272 A1 | 12/2007 |
|---|---|---|
| WO | WO 2006/108143 | 10/2006 |

OTHER PUBLICATIONS

International Search Report and Written Opinion of International Application No. PCT/US2017/014748, dated Apr. 10, 2017 (14 pages).

(Continued)

*Primary Examiner* — Alexandra L Newton
(74) *Attorney, Agent, or Firm* — Bookoff McAndrews, PLLC

(57) ABSTRACT

A medical device may include a sheath extending from a proximal end to a distal end. The medical device may further include a light source coupled to the sheath. The light source may have a first state in which light is not emitted distally of sheath and a second state where the light source emits a visual pattern distally of the distal end of the sheath. The visual pattern may represent a cross-sectional dimension of a structural feature of the sheath.

15 Claims, 4 Drawing Sheets

(52) U.S. Cl.
CPC .............. *A61B 1/0676* (2013.01); *A61B 1/07* (2013.01); *A61B 1/307* (2013.01); *A61B 17/2202* (2013.01); *A61B 90/30* (2016.02); *A61B 17/22031* (2013.01); *A61B 2017/22005* (2013.01); *A61B 2017/22079* (2013.01); *A61B 2090/061* (2016.02)

(58) Field of Classification Search
CPC .............. A61B 1/00165; A61B 1/0676; A61B 2018/00982; A61B 5/1072; A61B 1/00087; A61B 1/00135; A61B 1/00167; A61B 1/0684; A61B 1/0607; A61B 1/0615; A61B 18/20
See application file for complete search history.

(56) References Cited

U.S. PATENT DOCUMENTS

| | | | |
|---|---|---|---|
| 2009/0036739 A1* | 2/2009 | Hadani | A61B 1/00105 600/121 |
| 2009/0062782 A1* | 3/2009 | Brown | A61B 18/20 606/15 |
| 2015/0057570 A1* | 2/2015 | Chin | A61B 10/0283 600/566 |
| 2015/0272676 A1* | 10/2015 | Hasenberg | A61B 18/22 606/15 |
| 2015/0320433 A1* | 11/2015 | Navve | A61B 17/2256 606/2.5 |
| 2015/0351621 A1 | 12/2015 | Hill et al. | |
| 2015/0366571 A1 | 12/2015 | Navve et al. | |

OTHER PUBLICATIONS

Sorensen, Matthew D., et al., "Ureteroscopic Ultrasound Technology to Size Kidney Stone Fragments: Proof of Principle Using a Miniaturized Probe in a Porcine Model," Journal of Endourology, vol. 24, No. 6, Jun. 2010, pp. 939-942.

Dunmire, Barbrina, et al., "Use of the Acoustic Shadow Width to Determine Kidney Stone Size with Ultrasound," J Urol. 195(1): 171-177 Jan. 2016, 13 pages.

* cited by examiner

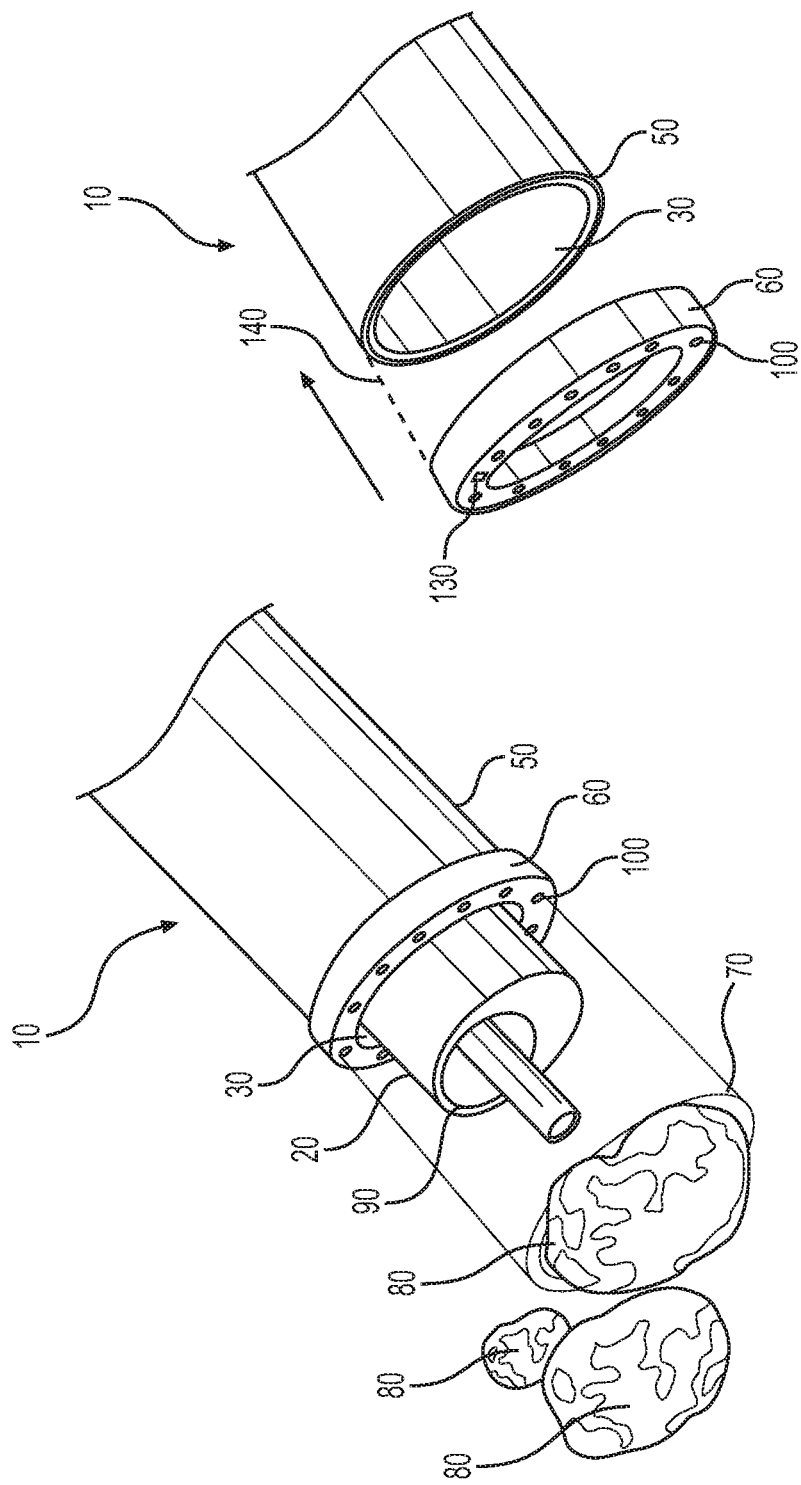

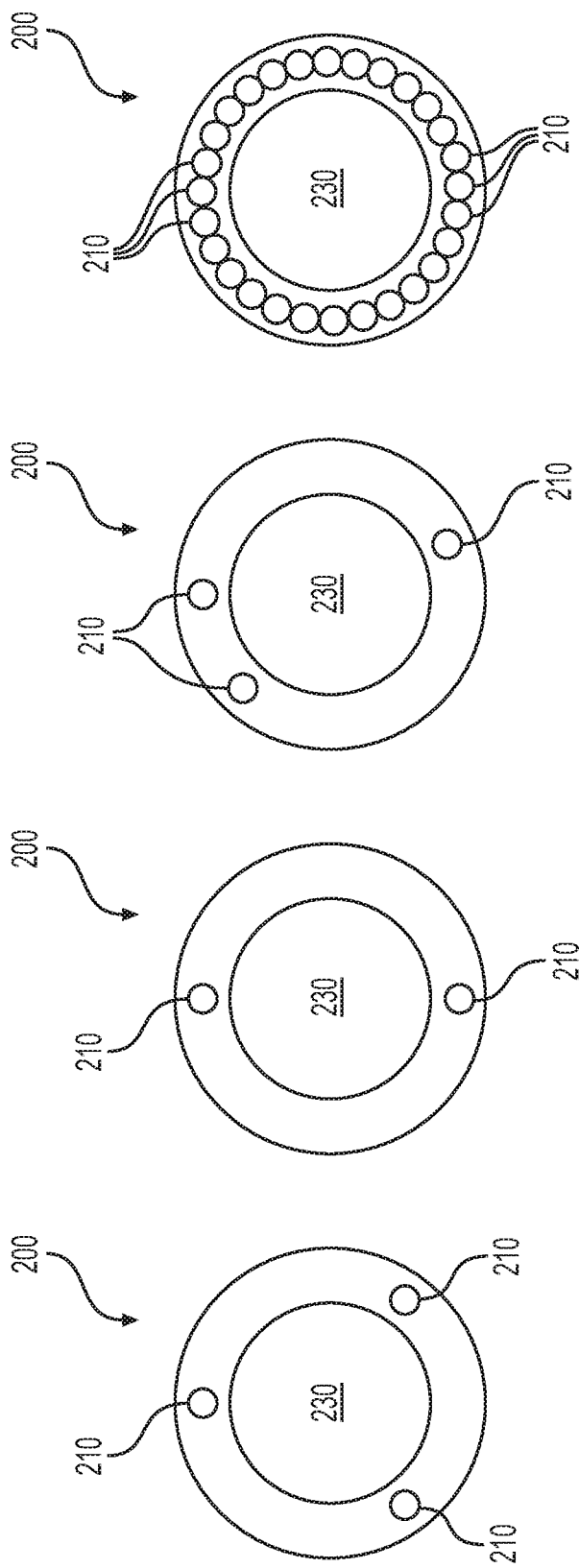

MEDICAL RETRIEVAL DEVICES AND RELATED METHODS OF USE

CROSS-REFERENCE TO RELATED APPLICATIONS

This patent application claims the benefit of priority under 35 U.S.C. § 119 to U.S. Provisional Patent Application No. 62/288,906, filed Jan. 29, 2016, which is herein incorporated by reference in its entirety.

TECHNICAL FIELD

Examples of the present disclosure relate generally to medical devices and procedures. In particular, embodiments of the present disclosure relate to medical devices and methods for extraction of tissue and/or other materials.

BACKGROUND

Medical retrieval devices including, for example, baskets and forceps, are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy (PNCL) procedure. Other procedures may include endoscopic retrograde cholangiopancreatography (ERCP), which is a procedure for treating the bile and pancreatic ducts of a patient. Further, lithotripsy and ureteroscopy, for example, are used to treat urinary calculi (e.g., kidney stones) in the ureter of a patient.

One problem commonly associated with retrieval of such concretions occurs where the stone or other material is too large to be removed through a sheath and/or a scope, e.g., ureteroscope, en bloc (e.g., whole and/or in one piece). For example, the stone or other material may be too large to pass through a lumen defined by the sheath (e.g., a renal sheath) and the working channel of such a ureteroscope. In such cases, a medical professional may be required to break up such stones and or other material so as to be small enough to pass through the sheath and/or the working channel of such a ureteroscope. Often, however, a medical professional may not be able to readily determine which stones or other material will be required to be broken up prior to removal through the sheath and/or working channel. Accordingly, the medical professional may deliver a retrieval device (e.g., a basket and/or forceps) through the working channel of the ureteroscope, capture the stone or other material in the retrieval device, and then attempt to retrieve the stone or other material through the sheath and/or scope, only to subsequently determine the stone or other material is too large to be retrieved through the working channel of the ureteroscope and/or the lumen of the sheath. Accordingly, the medical professional may be required to tediously determine which stones or other material must be broken up (e.g., via a lithotripter or the like) by a method of trial and error. Such a process may be time consuming and expensive.

SUMMARY

Examples of the present disclosure relate to, among other things, medical devices for use during retrieval, and related methods of use. Each of the examples disclosed herein may include one or more of the features described in connection with any of the other disclosed examples.

A medical device may include a sheath extending from a proximal end to a distal end. The medical device may further include a light source coupled to the sheath. The light source may have a first state in which light is not emitted distally of sheath and a second state where the light source emits a visual pattern distally of the distal end of the sheath. The visual pattern may represent a cross-sectional dimension of a structural feature of the sheath.

Aspects of the medical device may additionally and/or alternatively include one or more other features. The medical device may further include a visual guide coupled to the distal end of the sheath, and the light source may be disposed on the visual guide. The light source may include a plurality of light-emitting diodes. The plurality of light-emitting diodes may be equidistantly spaced about a circumference of the light guide. The plurality of light-emitting diodes may be non-equidistantly spaced about a circumference of the light guide. The medical device may further include a chip disposed on the visual guide, in which the chip may be configured to wirelessly communicate with an actuator positioned at a proximal end of the sheath to transition the light source between the first state and the second state. The visual guide may non-removably coupled to a distal end of the sheath. The visual guide may be removably coupled to the distal end of the sheath. The sheath may be comprised of light-guide material. The light source may include a plurality of optical fibers extending from the proximal end to the distal end of the sheath. The plurality of optical fibers may be monolithically formed with the sheath. The plurality of optical fibers may be equidistantly spaced about a circumference of the sheath. The plurality of optical fibers may be non-equidistantly spaced about a circumference of the sheath. The visual pattern may be ring-shaped and may have a diameter equal to the diameter of a lumen of the sheath. The cross-sectional dimension may be a diameter, and the structural feature may be a lumen.

In another example, a method of removing material from the body of a patient may include delivering a sheath to a location within the body of a patient. The sheath may have a proximal end and a distal end and may define a lumen therein. The method may further include actuating an actuator coupled to a proximal end of the sheath to cause a visual pattern to project distally of the sheath. The visual pattern may include visible light having a cross-sectional dimension corresponding to a cross-sectional dimension of a structural feature of the sheath. Further, the method may include measuring a size of material in the body via the visual pattern.

Aspects of the method may additionally and/or alternatively include one or more other features. The method may further include removing the material from the body of the patient through the lumen of the sheath. The method may further include delivering an insertion device through the lumen of the sheath. The method may also include delivering a lithotripter through a working channel of the insertion device and fragmenting the material. The sheath may include a visual guide coupled to the distal end of the sheath, and actuating an actuator may include illuminating a plurality of light-emitting diodes positioned about the visual guide.

In another example, a method of removing material from the body of a patient may include delivering a sheath to a location within the body of a patient. The sheath may have a proximal end and a distal end and defining a lumen therein.

The method may further include actuating an actuator coupled to a proximal end of the sheath. Actuating the actuator may cause a light source to transition between a first state in which light is not emitted distally of the sheath and a second state in which the light source emits a visual pattern distally of the distal end of the sheath. The visual pattern may be ring-shaped and may include a diameter corresponding to a diameter of a lumen of the sheath. Additionally, the method may include determining whether the material will fit within the lumen of the sheath via the visual pattern.

Aspects of the method may additionally and/or alternatively include one or more other features. The method may further include removing the material from the body of the patient through the lumen of the sheath. Further, the method may include delivering an insertion device through the lumen of the sheath, and delivering a lithotripter through a working channel of the insertion device and fragmenting the material.

It may be understood that both the foregoing general description and the following detailed description are exemplary and explanatory only and are not restrictive of the disclosure, as claimed.

As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" as used herein is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 1 illustrates an exemplary sheath and visual guide emitting a visual pattern;

FIG. 2 illustrates a perspective exploded view of the exemplary visual guide and sheath of FIG. 1;

FIGS. 6A-6D illustrate various end views of the exemplary visual guide of FIG. 1 or the distal end of the exemplary sheath of FIG. 5.

DETAILED DESCRIPTION

The terms "proximal" and "distal" are used herein to refer to the relative positions of the components of exemplary medical devices. When used herein, "proximal" refers to a position relatively closer to a user of a medical device. In contrast, "distal" refers to a position relatively farther away from the user of a medical device.

FIG. 1 illustrates an exemplary sheath 10 for insertion in a body passage. For example, sheath 10 may include any device configured to allow a user to access internal areas of a subject's body. Additionally or alternatively, sheath 10 may include any device configured to deliver an insertion device 20 therethrough, as will be described in further detail below. That is, sheath 10 may define a lumen 30 configured (e.g., sized and shaped) to receive insertion device 20 therethrough. For example, an internal diameter of sheath 10 may be between about 1-12 mm, about 4-10 mm, or about 7-10 mm. As used herein, the terms "about," "substantially," and "approximately," may indicate a range of values within +/−5% of a stated value.

Further, sheath 10 may have any appropriate cross-sectional shape. For example, as shown in FIG. 1, sheath 10 may have a circular cross-sectional shape. However, other cross-sectional shapes, such as ovular, irregular, and/or polygonal cross-sectional shapes are contemplated and are within the scope of this disclosure. Additionally or alternatively, in some examples, the cross-sectional shape and/or size of sheath 10 may vary along the length of sheath 10. For example, in some examples, a proximal portion may have an ovular cross-sectional shape while a distal portion may have a circular cross-sectional shape. Further, in some examples, the diameter of lumen 30 may be varied along the length of sheath 10. Additionally, sheath 10 may have a length of between about 10 and about 30 cm, about 15 and about 25 cm, or about 17 and about 20 cm.

Sheath 10 may include any appropriate biocompatible material, such as, for example, polymer, urethane, polyethylene terephthalate (PTE), polypropylene, acrylonitrile butadiene styrene (ABS), polyurethane, polyterafluoroetheylene (PTFE), PTE clear plastic, fluoro-polymer blends, metals (e.g., stainless steel) and the like. In one example, sheath 10 may have a flexibility that is sufficient to allow passage of sheath 10 through a bodily tract or opening (e.g., natural opening(s) or opening(s) made by a medical professional) in a patient's body. For example, sheath 10 may have a flexibility that is sufficient to allow passage of sheath 10 through the urethra and across the bladder of the patient. In such an arrangement, sheath 10 may be a renal sheath. Sheath 10 may be sterile, single-use, and disposable. In other arrangements, however, sheath 10 may be a multiple-use sheath 10 and may be non-disposable.

Figure 3:
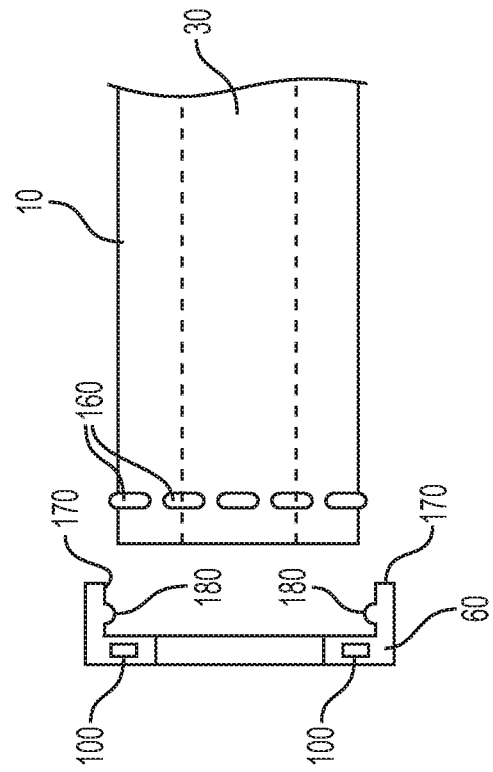
FIG. 3 illustrates a side-view of the exemplary visual guide and sheath of FIGS. 1 and 2, having a snap-fit arrangement.

Sheath 10 may extend from a proximal end 40 (FIG. 4) to a distal end 50 and define lumen 30 therethrough. Distal end 50 of sheath 10 may include a visual guide 60 coupled thereto. Visual guide 60 may be generally circular. That is, visual guide 60 may include a cross-sectional shape similar to or corresponding to the cross-sectional shape of sheath 10. For example, a cross-sectional shape of visual guide 60 may be circular, ovular, irregular, and/or polygonal depending on the cross-sectional shape of sheath 10. As shown, visual guide 60 may be constructed as an annulus (e.g., doughnut). For example, visual guide 60 may define a central opening aligned with lumen 30 of sheath 10. In such a manner, stones 80 or other material may pass through the central opening of visual guide 60 into lumen 30 of sheath 10. In the case of a single-use disposable sheath 10, visual guide 60 may be non-seperably (e.g., permanently) attached to distal end 50, as shown in FIG. 1. For example, as discussed in further detail below, in some arrangements, visual guide 60 may be monolithically formed with sheath 10. Alternatively, in some arrangements, visual guide 60 may be attached to distal end 50 of insertion device 20 via any appropriate adhesive or the like. In the case of a non-disposable, multiple-use sheath 10, visual guide 60 may be selectively coupled (e.g., via a snap-fit connection) and uncoupled from distal end 50 as shown in FIG. 3, as will be described in further detail below.

As shown in FIG. 1, visual guide 60 may be configured to emit a visual pattern 70. Such a visual pattern 70, as shown in FIG. 1, for example, may be comprised of one or more zones or regions of visible light (e.g., electromagnetic radiation having a frequency between about 430 THz and about 770 THz) forming a generally circular (e.g., a ring) pattern. That is, in some arrangements, visual pattern 70 may correspond (e.g., be similar) in shape to distal end 50. In some arrangements, however, visual pattern 70 may form a different or non-corresponding shape than distal end 50, as will be described in further detail below.

Visual pattern 70 may comprise a visual representation of the size and/or shape of sheath 10 and/or lumen 30 of sheath 10. That is, visual pattern 70 may enable a medical professional to readily determine whether a particular stone 80 or other material is of a size small enough to pass through lumen 30 of sheath 10. For example, in use, a medical professional may actuate or otherwise cause (as will be described in further detail below) visual guide 60 to emit visual pattern 70. Once emitted, a medical professional may direct sheath 60 toward one or more stones 80 or other material, or may direct a stone 80 (e.g., via insertion device 20) towards visual pattern 70. Upon locating stone 80 or other material near visual pattern 70, a medical professional may readily determine whether stone 80 or other material is smaller than and/or otherwise fits within an area circumscribed by visual pattern 70, and therefore also fits within lumen 30 by having a diameter and/or greatest cross-sectional dimension less than a diameter of lumen 30. If yes, a medical professional may readily remove such a stone 80 or other material through lumen 30 of sheath 10, and if small enough, through a working channel of insertion device 20. If, however, stone 80 or other such material is larger or shaped in a manner so as to not fit within the area circumscribed by visual pattern 70, the medical professional will understand that the stone 80 or other material must be fragmented prior to removal through sheath 10. Accordingly, rather than stopping a procedure to fragment the stone 80 or other material, the medical professional may proceed to the next stone 80 or other material to gauge the size of the next stone 80 or other material. After removal of all stones 80 or other material that are smaller or shaped in a manner so as to fit within the area circumscribed by visual pattern 70, and therefore within lumen 30 or working channel 90 of insertion device 20, the medical professional may deliver a lithotripter or other such device through a working channel of insertion device 20 and/or lumen 30 of sheath 10, and may fragment any stones 80 or other material too large to pass through lumen 30. In such a manner, a medical professional may readily determine which stones 80 or other material must be fragmented prior to removal through sheath 10 such that tedious trial and error methods are unnecessary.

Insertion device 20 may include any device configured to allow a user to perform medical diagnoses and/or treatments on a subject. For example, insertion device 20 may include any device configured to allow a user to access and view internal areas of a subject's body. Additionally or alternatively, insertion device 20 may include any device configured to deliver medical instruments, such as, for example, biopsy forceps, graspers, baskets, snares, probes, scissors, retrieval devices, lasers, and/or other tools, into a subject's body. Insertion device 20 may be inserted into a variety of body openings, lumens, and/or cavities through sheath 10. For example, insertion device 10 may be inserted into any portion of a urinary tract, such as a ureter, a gastrointestinal lumen, such as an esophagus, a vascular lumen, and/or an airway.

According to aspects of the present disclosure, insertion device 20 may be a ureteroscope. In some contemplated examples, insertion device 20 may be a sterile, single-use, and disposable ureteroscope. Alternatively, insertion device 20 may be a multiple-use, non-disposable ureteroscope. Other types of devices, however, may be substituted for the ureteroscope, including, as examples, an endoscope, a hysteroscope, a uteroscope, a colonoscope, a bronchoscope, a cystoscope, and similar devices. Such devices may be single-use and disposable, or multiple-use and non-disposable.

Insertion device 20 may include at least one working channel 90 as shown in FIG. 1. According to some aspects, insertion device 20 may include two or more working channels 90. Further, working channels 90 may have different shapes and/or sizes. For example, a first working channel 90 may be relatively larger than at least one other working channel 90. Alternatively, in some arrangements, each working channel, if more than one working channel is included, may be equally sized. In some arrangements, insertion device 20 may include one or more electronic components, such as a camera or other imaging device, a light source, and/or other sensor. Additionally or alternatively, insertion device 20 may include a lumen for light delivery. Further, in some arrangements, insertion device 20 may be steerable. Accordingly, insertion device 20 may include a steering mechanism having one or more steering control members (e.g., wires, cables, etc.) positioned within one or more control channels (not shown) to house the steering control members.

In some aspects of the present disclosure, a handle (not shown) of insertion device 20 may include at least one port (not shown) in communication with working channel 90 to allow for the insertion of tools (e.g., forceps, scissors, a grasper, a snare, a probe, a guidewire, a laser, an optical device, an imaging device). Optionally, insertion device 20 may further include one or more irrigation and/or aspiration channels (not shown). The handle may also include an electronics hub (not shown) or connector for electrical connections, such as for transferring data and/or powering a light source.

Figure 4:
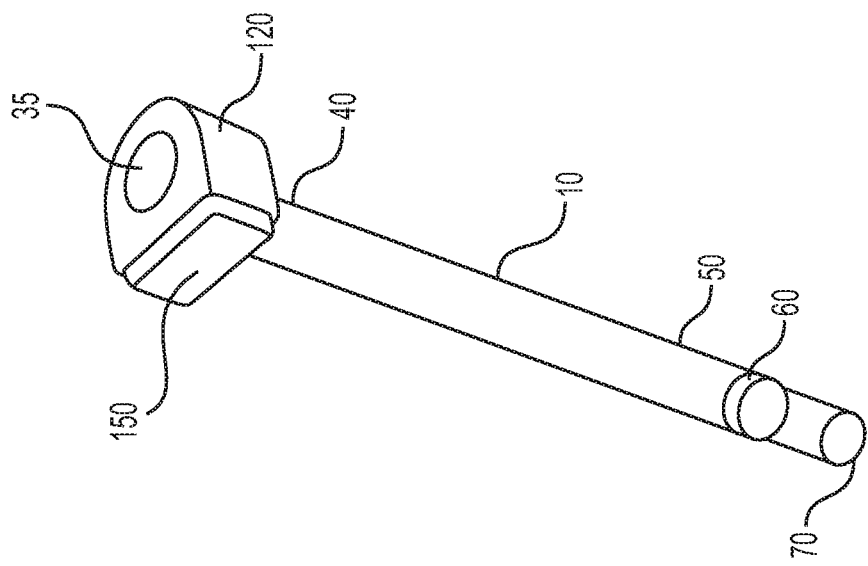
FIG. 4 illustrates a perspective view of an exemplary handle coupled to the sheath of FIG. 1.

Visual guide 60 may include any appropriate components and/or structure configured to emit visual pattern 70. For example, in some arrangements, as shown in FIG. 2, visual guide 60 may include one or more light-emitting diodes (LEDs) 100. For example, LEDs 100 may be disposed about visual guide 60. LEDs 100 may be arranged about visual guide 60 equidistantly and/or non-equidistantly (e.g., irregularly). LEDs 100 may be operably coupled so as to wirelessly communicate with an actuator 150 of a handle 120 (FIG. 4) via a wireless chip 130 or other such device. Alternatively, LEDs 100 may be coupled to actuator 150 via a wired connection 140. For example, wired connection 140 may extend from visual guide 60, along sheath 10 toward handle 120 and may be operably coupled to actuator 150. In either manner of connection, actuation of actuator 150 may cause LEDs 100 to illuminate and or emit visual pattern 70. Actuator 150 may include any appropriate construction configured to adjust a state (e.g., emitting or not emitting visual pattern 70) of visual guide 60. For example, actuator 150, as shown in FIG. 4, may include a button or other depressible member. However, the disclosure is not limited to such arrangements. Rather, actuator 150 may include any appropriate construction including triggers, switches, rockers, rotatable wheels, joy-sticks and the like.

As noted above, in some arrangements, visual guide 60 may be selectively coupled (e.g., via a snap-fit connection) and uncoupled from distal end 50 of sheath 10. Accordingly, as shown in FIG. 3, distal end 50 of sheath 10 may include one or more raised protrusions and/or extension(s) 160 extending from an exterior circumferential surface of sheath 10. Additionally, visual guide 60 may include a proximally extending lip 170. Lip 170 may be generally flexible. That is, lip 170 may be thin relative to a dimension of visual guide 60. Accordingly, lip 170 may be spread or bent radially outwardly of a central longitudinal axis of sheath 10. Additionally, lip 170 may include one or more protrusions and/or bump(s) 180 extending radially inwardly from an interior surface of lip 170.

Accordingly, in use, visual guide 60 may be snap-fit onto distal end 50 of sheath 10 via the interaction between bump(s) 180 of lip 170 and extension(s) 160. That is, visual guide 60 may be positioned proximate distal end 50, and caused (e.g., urged, pushed, or forced) to be placed on distal end 50. Such a force may be sufficient to bend or deflect lip 170 radially outwardly of a central longitudinal axis of sheath 10. As visual guide 60 is pushed or forced onto distal end 50, bump(s) 180 may be guided or driven over extension(s) 160. Once bump(s) 180 pass the apex of extension(s) 160, lip 170 may snap radially inwards toward the central longitudinal axis of sheath 10. Accordingly, in such a manner, visual guide 60 may be retained on a distal end of sheath 10 in a snap-fit arrangement. It is to be understood that extension(s) 160 and bump(s) 180 may have any appropriate configuration. For example, each of bumps 180 and extensions 160 may include a plurality of discontinuous bumps 180 and extensions 160, respectively, as shown. Alternatively, however, bumps 180 may include a single continuous bump 180 extending along an interior surface of lip 170. Additionally or alternatively, extensions 160 may include a single continuous extension 160 extending along the exterior circumferential surface of sheath 10. In either arrangement, visual guide 60 may be retained on a distal end of sheath 10 in a snap-fit arrangement.

As discussed above, visual guide 60 may include a plurality of LEDs 100 configured to emit visual pattern 70. However, in some arrangements, sheath 10 may itself be a light guide. For example, sheath 10 may include and/or be made of one or more of an optical grade material such as, for example, acrylic resin, polycarbonate, epoxies, and/or glass. Such a light guide may transport light from a light source (not shown) positioned within or attached to handle 120 by means of total internal reflection. Accordingly, rather than attaching or including visual guide 60 at the distal end of sheath 10, sheath 10 may itself transmit light from a light source (not shown) positioned within or attached to handle 120, through sheath 10 and emit visual pattern 70 distally of distal end 50 of sheath 10.

Figure 5:
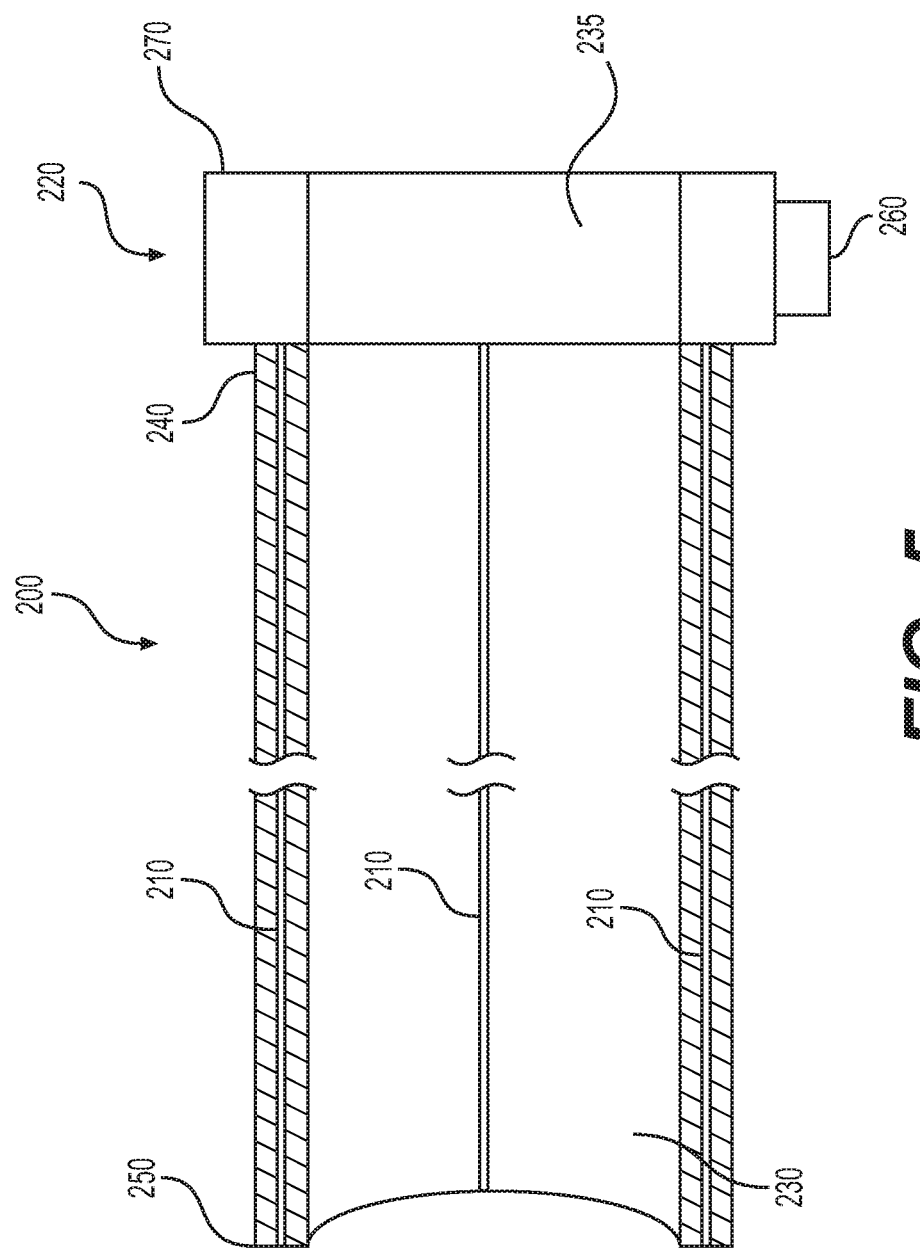
FIG. 5 illustrates a side cross-sectional view of an exemplary sheath including a plurality of optical fibers according to a further arrangement.

Alternatively, in some arrangements, sheath 10 may be provided with one or more optical fibers. For example, as shown in FIG. 5, a sheath 200 may be similar to sheath 10, and further include one or more optical fibers 210 extending therethrough. For example, sheath 200 may include any device configured to allow a user to access internal areas of a subject's body, and/or may include any device configured to deliver an insertion device 20 (FIG. 1) therethrough. That is, sheath 200 may define a lumen 230 configured (e.g., sized and shaped) to receive insertion device 20 therethrough. Further, sheath 200 may have any appropriate cross-sectional shape, such as, for example, circular, ovular, irregular, and/or polygonal. Additionally or alternatively, in some examples, the cross-sectional shape and/or size of sheath 200 may vary along the length of sheath 200. Sheath 10 may include any appropriate biocompatible material having any necessary or desired rigidity that is sufficient to allow passage of sheath 200 through a bodily tract or opening in a patient's body.

Sheath 200 may extend from a proximal end 240 to a distal end 250 and define lumen 230 therethrough. As shown, optical fibers 210 may extend along sheath 200 from proximal end 240 to distal end 250. That is, optical fibers 210 may extend along the entire length of sheath 200. A proximal end of each optical fiber 210 may be operably coupled with an actuator 260 of a handle 270. For example, actuation of actuator 260 may cause optical fibers 210 to illuminate and or emit visual pattern 70 (FIGS. 1 and 4). Actuator 260 may include any appropriate construction configured to adjust a state (e.g., emitting or not emitting visual pattern 70) of optical fibers 210.

In some arrangements, optical fibers 210 may be co-extruded with sheath 200. In such a manner, optical fibers 210 may be monolithically formed with sheath 200. In such a manner, a separate visual guide 60 may be unnecessary. Rather, optical fibers 210 themselves may emit visual pattern 70 from a distal end thereof. Alternatively, in some arrangements, sheath 200 may include channels (not shown) extending between a radially interior surface and a radially exterior surface of sheath 200. Each channel may be configured to receive one or more optical fibers 210 therein.

As discussed above, visual pattern 70 may be generally circular (e.g., a ring). In some arrangements, however, visual pattern 70 may not be circular. For example, FIGS. 6A-6D illustrate various exemplary arrangements of optical fibers 210 about sheath 200. For example, as shown in FIG. 6A, three optical fibers 210 may be disposed equidistant (e.g., a centerline of each optical fiber 210 may be spaced about 120° apart from a centerline of an adjacent optical fiber 210) about sheath 200. In such a manner, optical fibers 210 may collectively emit three zones or regions of light in a generally triangular shape. That is, each fiber 210 may emit a zone or region of light along a corner of an equilateral triangular shaped visual pattern 70.

Alternatively, as shown in FIG. 6B, two optical fibers 210 may be disposed equidistant (e.g., a centerline of each optical fiber 210 may be spaced about 180° apart from a centerline of an adjacent optical fiber 210) about sheath 200. In such a manner, optical fibers 210 may collectively emit two zones or regions of light in a generally linear shape. That is, each fiber 210 may emit a zone or region of light along an end of a linearly shaped visual pattern 70.

In an alternative arrangement, as shown in FIG. 6C, three optical fibers 210 may be disposed non-equidistantly about sheath 200. In such a manner, optical fibers 210 may collectively emit three zones or regions of light in a generally triangular shape. That is, each fiber 210 may emit a zone or region of light along a corner of an isosceles triangular shaped visual pattern 70. While FIG. 6C illustrates optical fibers 210 arranged to produce three zones or regions of light along a corner of an isosceles triangular shaped visual pattern 70, it is understood that such a representation is merely explanatory. Rather, optical fibers 210 may be arranged in any non-equidistant arrangement so as to emit a zone or region of light along a corner of any non-equilateral (e.g., scalene, obtuse, acute, right, and/or isosceles) triangle.

In a further arrangement, any number of appropriate optical fibers 210 may be disposed about sheath 200. For example, in some arrangements, as many optical fibers 210 as will fit may be disposed about sheath 200. For example, as shown in FIG. 6D, 28 optical fibers 210 are positioned about sheath 200. As shown, due to the large number of optical fibers 210, each optical fiber 210 is tightly packed (e.g., abuts or is minimally spaced) from an adjacent optical fiber 210. While 28 optical fibers 210 are shown in FIG. 6D, the disclosure is not so limited. Rather, any appropriate number of optical fibers 210, as space allows, may be positioned along sheath 200. For example, sheath 200 may include between about 2 and about 100, between about 10 and about 80, and between about 40 and about 60 optical fibers 210 disposed about sheath 200, depending on the size (e.g., diameter) of sheath 200 and the size (e.g., diameter) of optical fibers 210. In some arrangements, sheath 200 may have an outer diameter between about 2 and about 10 mm, between about 3 and about 8 mm, or between about 4 and about 7 mm. Additionally, the diameter of each optical fiber 210 may be between about 50 and about 1000 microns, between about 100 and about 800 microns, or between about 300 and about 600 microns. Further, in some arrangements, sheath 200 may have a diameter of about 30 French (1 cm), a wall thickness (between a radially inner surface and a radially outer surface of about 0.35 inches (0.889 cm), and may include about 50 optical fibers 210 each having a diameter of about 0.025 inches (0.635 mm). It is understood that the greater the number of optical fibers 210 disposed about sheath 200, the higher degree of accuracy a medical professional may be provided to gauge the size of stones 80 or other material. For example, the greater the number of optical fibers 210, the fewer or smaller the inconsistencies, e.g., spaces between adjacent optical fibers 210, and consequently, between zones or regions of light in visual pattern 70. While FIGS. 6A-6D are discussed and illustrated in connection with an arrangement including optical fibers 210, it is to be understood that similar concepts may apply to LEDs 100. That is, LED's 100 may be positioned about visual guide 60 in a manner similar to the arrangements shown in FIGS. 6A-6D.

Accordingly, in use, a medical professional may deliver sheath 10, 200 to an area of interest within a patient. Once so delivered, the medical professional may deliver insertion device 20 through a port 35 or 235 positioned on handle 120 or 220, respectively (FIGS. 4 and 5). One inserted through port 35 or 235, insertion device 20 may be advanced distally through lumen 30 or 230 of sheath 10 or 200, respectively. It is understood that in some arrangements, sheath 10 or 200 may be delivered simultaneously with insertion device 20 (e.g., insertion device 20 may be positioned within lumen 30 or 230 prior to insertion of sheath 10 or 200 into the body of the patient). Once in position, the medical professional may actuate actuator 150 or 260 on handle 120 or 270 so as to adjust a state of LEDs 100, a light source, and/or optical fibers 210. That is, actuator 150 or 260 may be actuated so as to cause LEDs 100, a light source (not shown) in communication with sheath comprised of light guide material, and/or optical fibers 210 to transition from a first "off" state to a second "on" state in which the LEDs 100, light source, and/or optical fibers 210 emit or produce visible light, and consequently, visual pattern 70.

Once visual pattern 70 is produced, a medical professional may view an area of interest within the patient. For example, the medical professional may utilize the camera or other such imaging device of insertion device 20 to view the area of interest and locate stones 80 or other material to be removed from the body of the patient. Next, the medical professional may direct sheath 10 or 200 toward one or more stones 80 or other material, or may direct a stone 80 (e.g., via insertion device 20) towards visual pattern 70. Upon locating stone 80 or other material near visual pattern 70, a medical professional may readily determine whether stone 80 or other material is smaller than and/or fits within an area circumscribed by visual pattern 70. If yes, a medical professional may readily remove such a stone 80 or other material through lumen 30 or 230 of sheath 10 or 200, respectively, and if small enough, through a working channel 90 of insertion device 20. For example, if it is determined that stone 80 or other material to be removed fits within the area circumscribed by visual pattern 70, the medical professional may deliver a tool (e.g., forceps, snare, and/or basket) (not shown) through working channel 90 of insertion device and capture stone 80 and/or other material therein. Upon capture, the medical professional may proximally retract the tool toward sheath 10 or 200 and into lumen 30 or 230, respectively. Further proximal retraction of the tool toward the sheath may cause the tool to proximate insertion device 20. Upon retraction, if stone 80 and/or other material hits, abuts, or otherwise impacts a distal end face of insertion device 20 because stone 80 and/or other material is too large to pass through working channel 90 of insertion device 20, then the medical professional may retract insertion device 20 along with the tool, and consequently, the captured stone 80 and/or other material simultaneously, while leaving sheath 10 or 200 in place within the patient. Regardless of whether stone 80 is smaller than the area circumscribed by visual pattern 70 but larger than working channel 90, or stone 80 is smaller than the area circumscribed by visual pattern 70 but smaller than working channel 90, stone 80 or other material may be removed without fragmenting stone 80 or other material and while leaving sheath 10 or 200 in place in the body of the patient.

If, however, stone 80 or other such material is larger or shaped in a manner so as to not fit within the area circumscribed by visual pattern 70, the medical professional will understand that the stone 80 or other material must be fragmented prior to removal through lumen 30 or 230 of sheath 10 or 200, respectively. Accordingly, rather than stopping a procedure to fragment the stone 80 or other material, the medical professional may proceed to the next stone 80 or other material to gauge the size of the next stone 80 or other material. After removal of all stones 80 or other material that are smaller or shaped in a manner so as to fit within the area circumscribed by visual pattern 70, the medical professional may deliver a lithotripter or other such device through working channel 90 of insertion device 20 and/or lumen 30, 230 of sheath 10, 200, and may fragment any stones 80 or other material too large to pass through lumen 30, 230. In such a manner, a medical professional may readily determine which stones 80 or other material must be fragmented prior to removal through sheath 10 or 200 such that tedious trial and error methods are unnecessary.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method of removing material from the body of a patient, the method comprising:
   delivering a sheath to a location within the body of the patient, the sheath having a proximal end and a distal end and defining a lumen therein;
   visualizing an area of interest via an imaging device to locate the material in the body of the patient;
   actuating an actuator coupled to the proximal end of the sheath to cause a visual pattern to project distally of the sheath via a light source removably coupled to the distal end of the sheath and including a plurality of light-emitting diodes, the visual pattern including visible light having a cross-sectional dimension corresponding to a cross-sectional dimension of a structural feature of the sheath and forming a continuous shape;

measuring a size of the material in the body via the visual pattern;

delivering an insertion device through the lumen of the sheath; and delivering a lithotripter through a working channel of the insertion device and fragmenting the material.

2. The method of claim 1, further comprising:

removing the material from the body of the patient through the lumen of the sheath.

3. The method of claim 1, wherein the light source is included on a visual guide coupled to the distal end of the sheath, wherein actuating the actuator includes illuminating the plurality of light-emitting diodes positioned about the visual guide.

4. The method of claim 1, wherein the light source is coupled to the distal end of the sheath via a snap-fit connection.

5. A method of removing material from the body of a patient, the method comprising:

delivering a sheath to a location within the body of the patient, the sheath having a proximal end and a distal end and defining a lumen therein;

visualizing an area of interest via an imaging device to locate the material in the body of the patient;

actuating an actuator coupled to the proximal end of the sheath, wherein actuating the actuator causes a light source to transition between a first state in which light is not emitted distally of the sheath and a second state wherein the light source emits a visual pattern distally of the distal end of the sheath, wherein the visual pattern is ring-shaped and includes a diameter corresponding to a diameter of the lumen of the sheath;

determining whether the material will fit within the lumen of the sheath via the visual pattern;

delivering an insertion device through the lumen of the sheath; and delivering a lithotripter through a working channel of the insertion device and fragmenting the material.

6. The method of claim 5, further including removing the material from the body of the patient through the lumen of the sheath.

7. The method of claim 5, wherein the light source is coupled to the distal end of the sheath via a snap-fit connection.

8. The method of claim 5, wherein the light source includes a plurality of light-emitting diodes, wherein the plurality of light-emitting diodes are spaced equidistantly about a circumference of the light source.

9. A method of removing material from the body of a patient, the method comprising:

delivering a sheath to a location within the body of the patient, the sheath having a proximal end and a distal end and defining a lumen therein;

visualizing an area of interest via an imaging device to locate the material in the body of the patient;

actuating an actuator coupled to the proximal end of the sheath, wherein actuating the actuator causes a light source removably coupled to the distal end of the sheath to transition between a first state in which light is not emitted distally of the sheath and a second state wherein the light source emits a visual pattern distally of the distal end of the sheath, wherein the visual pattern includes a dimension corresponding to a dimension of the lumen of the sheath;

determining whether the material will fit within the lumen of the sheath via the visual pattern;

delivering an insertion device through the lumen of the sheath; and delivering a lithotripter through a working channel of the insertion device and fragmenting the material.

10. The method of claim 9, further comprising:

removing the material from the body of the patient through the lumen of the sheath.

11. The method of claim 9, wherein the light source includes a plurality of light-emitting diodes.

12. The method of claim 11, wherein the plurality of light-emitting diodes are arranged in the shape of a ring such that the visual pattern includes a diameter corresponding to a diameter of the lumen of the sheath.

13. The method of claim 11, wherein the plurality of light-emitting diodes are spaced equidistantly about a circumference of the light source.

14. The method of claim 9, wherein the light source is coupled to the distal end of the sheath via a snap-fit connection.

15. The method of claim 9, wherein determining whether the material will fit within the lumen of the sheath via the visual pattern includes estimating a size of the material in the body via the visual pattern.

* * * * *